United States Patent
Spinelli et al.

(10) Patent No.: US 8,637,726 B2
(45) Date of Patent: *Jan. 28, 2014

(54) SHAPE AND PRESSURE ADJUSTABLE DRESSING

(75) Inventors: Thomas Spinelli, Northport, NY (US); Jahangir S. Rastegar, Stony Brook, NY (US)

(73) Assignee: Omnitek Partners LLC, Ronkonkoma, NY (US)

( * ) Notice: Subject to any disclaimer, the term of this patent is extended or adjusted under 35 U.S.C. 154(b) by 81 days.

This patent is subject to a terminal disclaimer.

(21) Appl. No.: 12/983,314

(22) Filed: Jan. 2, 2011

(65) Prior Publication Data

US 2012/0172778 A1 Jul. 5, 2012

(51) Int. Cl.
- *A61F 13/00* (2006.01)
- *A61L 15/16* (2006.01)
- *A61B 17/08* (2006.01)

(52) U.S. Cl.
USPC .............................. 602/53; 424/446; 606/216

(58) Field of Classification Search
USPC ............... 602/41–59; 604/304–308; 424/400, 424/443, 447–449
See application file for complete search history.

(56) References Cited

U.S. PATENT DOCUMENTS

| | | | |
|---|---|---|---|
| 4,605,005 A * | 8/1986 | Sheehan | 606/216 |
| 4,706,661 A | 11/1987 | Barrett | |
| 4,815,468 A | 3/1989 | Annand | |
| 4,865,026 A | 9/1989 | Barrett | |
| 5,630,430 A | 5/1997 | Shultz et al. | |
| 6,306,485 B1 | 10/2001 | Keller | |
| 6,838,589 B2 | 1/2005 | Liedtke et al. | |
| 6,916,967 B2 * | 7/2005 | Wright et al. | 602/42 |
| 7,122,712 B2 | 10/2006 | Lutri et al. | |
| 7,834,232 B2 * | 11/2010 | Rastegar et al. | 606/216 |
| 8,183,428 B2 * | 5/2012 | Gurtner et al. | 602/50 |
| 2003/0150449 A1 | 8/2003 | Spinelli et al. | |
| 2007/0282236 A1 | 12/2007 | LaGreca | |
| 2008/0146982 A1 | 6/2008 | Rastegar et al. | |
| 2008/0167593 A1 | 7/2008 | Fleischmann | |
| 2008/0306456 A1 | 12/2008 | Riesinger | |
| 2010/0318052 A1 | 12/2010 | Ha et al. | |

OTHER PUBLICATIONS

U.S. Office Action Dated Oct. 13, 2009 in related U.S. Appl. No. 11/998,926 (Issued as 7,834,232).
U.S. Office Action Dated Jan. 21, 2009 in related U.S. Appl. No. 11/998,926 (Issued as 7,834,232).
International Search Report Dated Dec. 4, 2012 received in corresponding International Application No. PCT/GB2012/052256.
International Search Report Dated Dec. 4, 2012 received in corresponding International Application No. PCT/GB2012/052258.

* cited by examiner

*Primary Examiner* — Patricia Bianco
*Assistant Examiner* — Tarla Patel

(57) ABSTRACT

A dressing for covering a wound in which the dressing includes: a first component having a first shape with a first dimension; a second component releasably attached to a first surface of the first component to maintain the first component in a second shape different from the first shape, the second shape having a second dimension longer than the first dimension; and an adhesive disposed on a surface of the first component different from the first surface for attaching the first component to the wound such that the second component can be released from the first component to allow the first component to take the first shape to apply a pressure to portions of the skin surrounding the wound to close the wound.

12 Claims, 7 Drawing Sheets

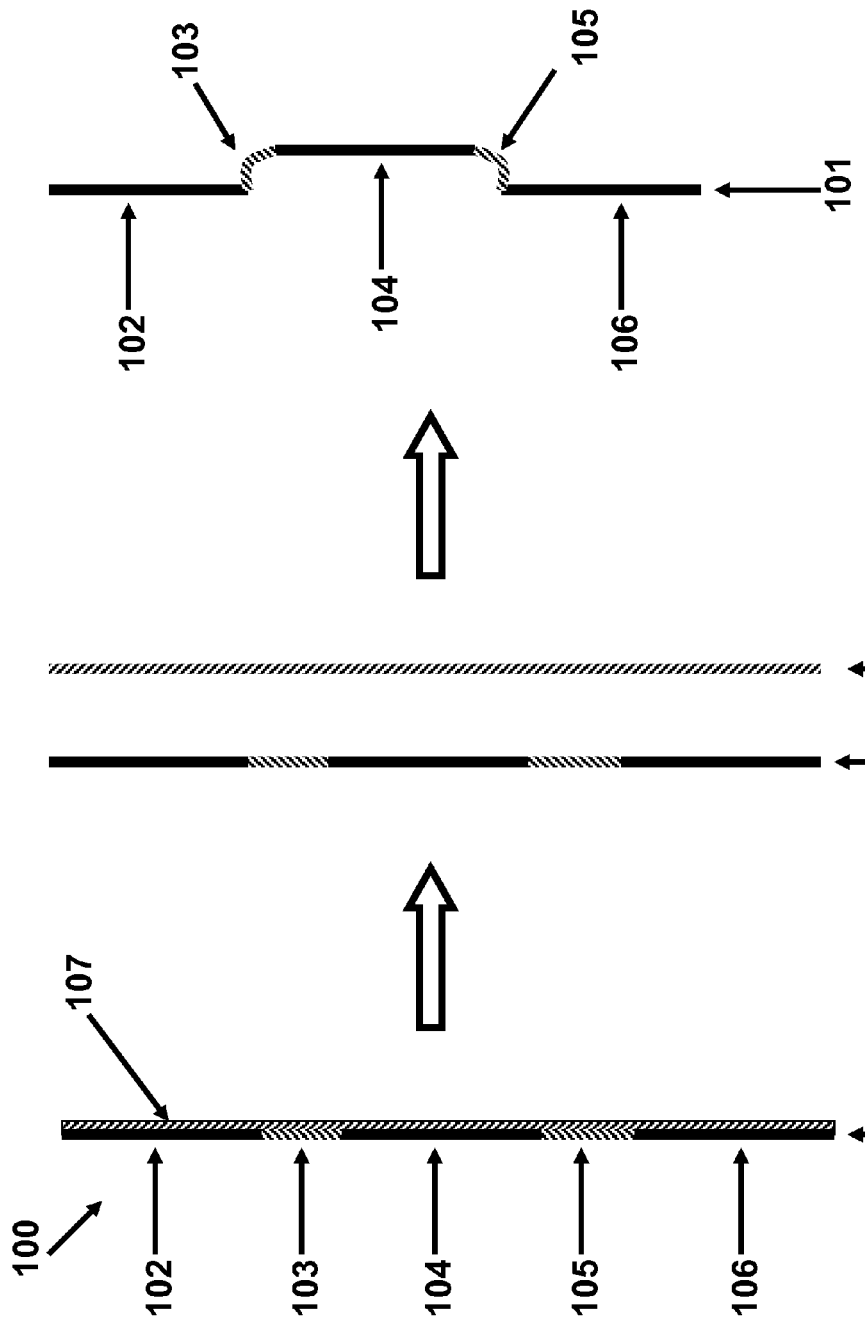

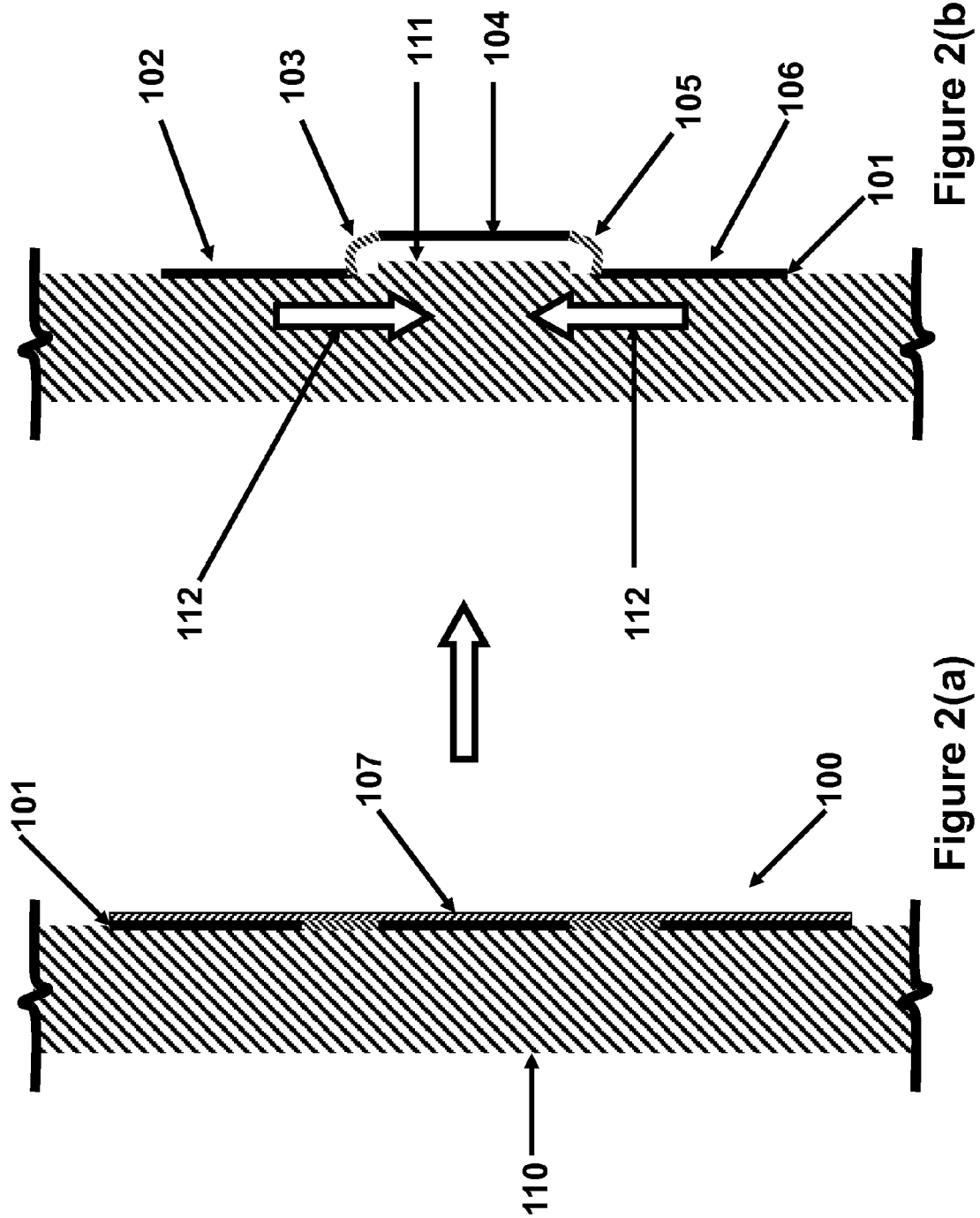

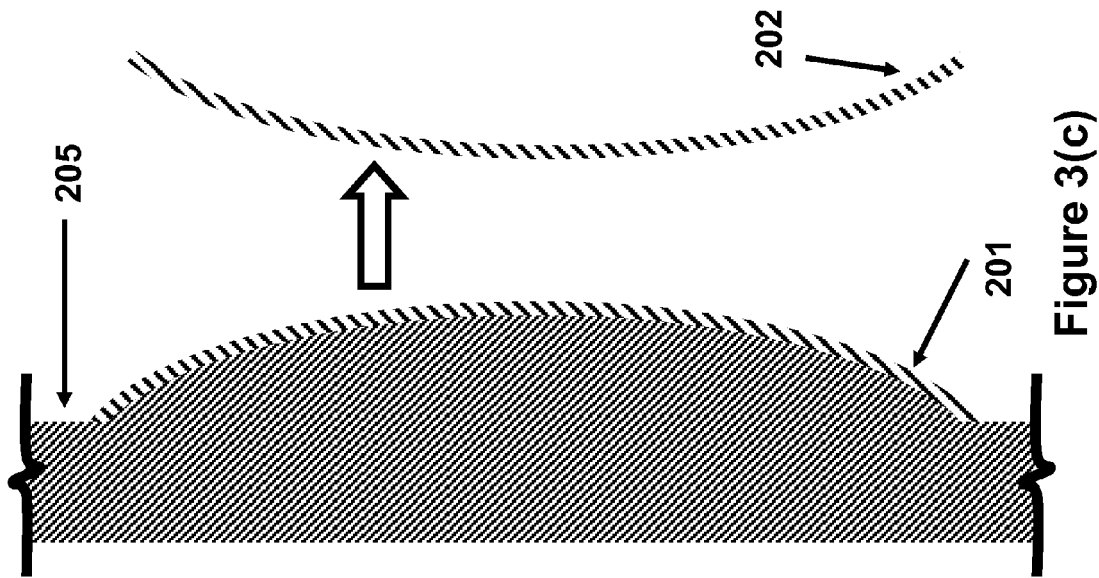
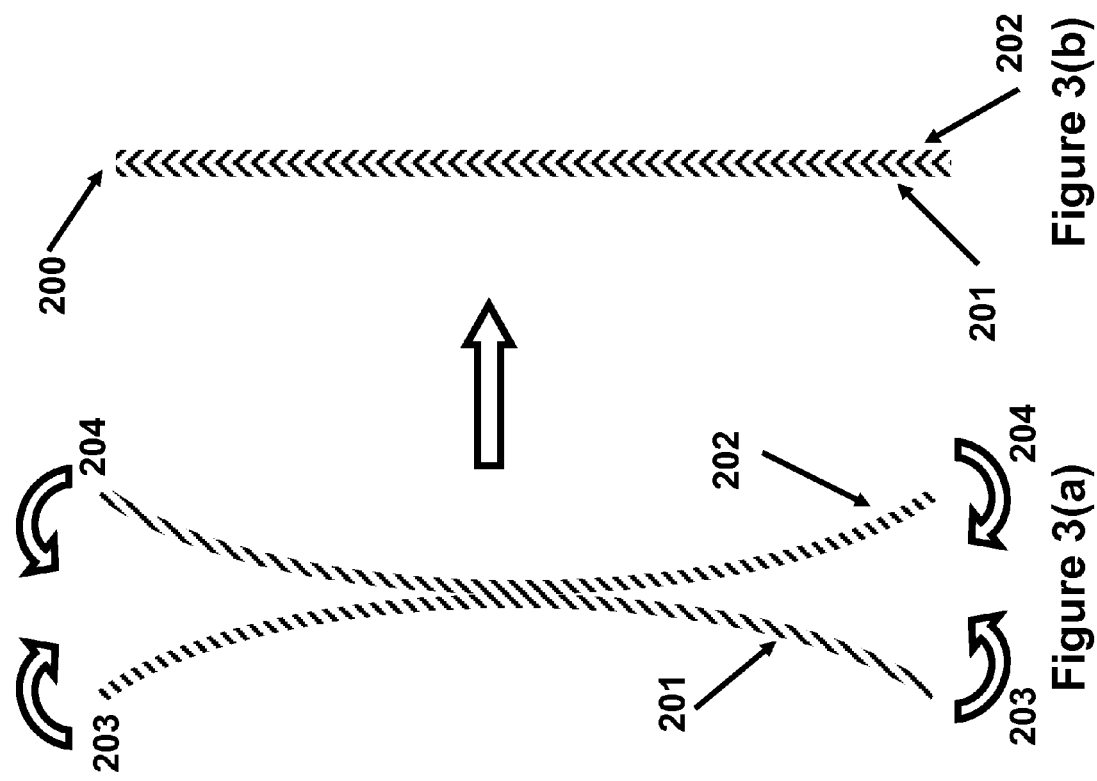
Figure 3(a)
Figure 3(b)
Figure 3(c)

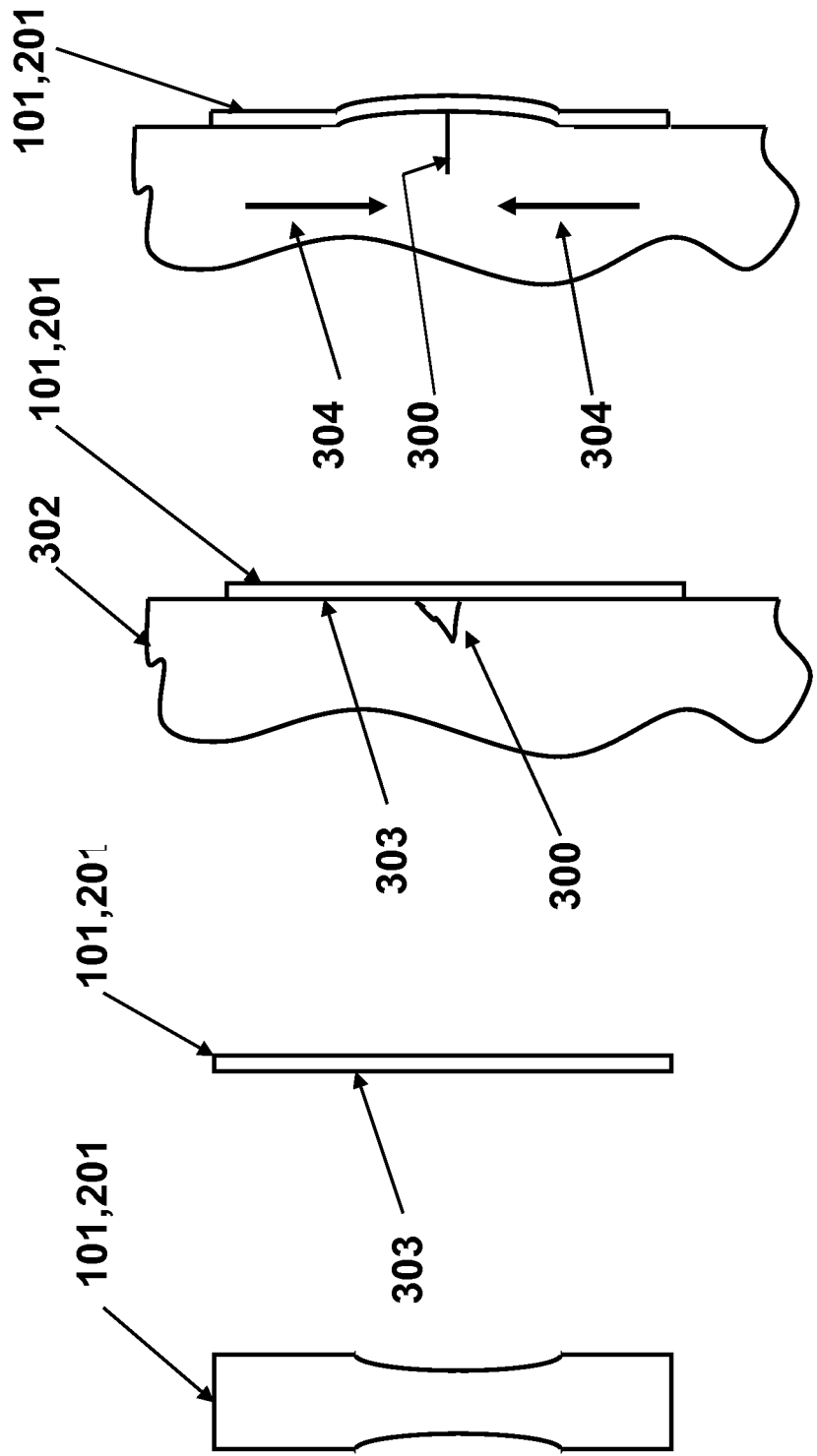

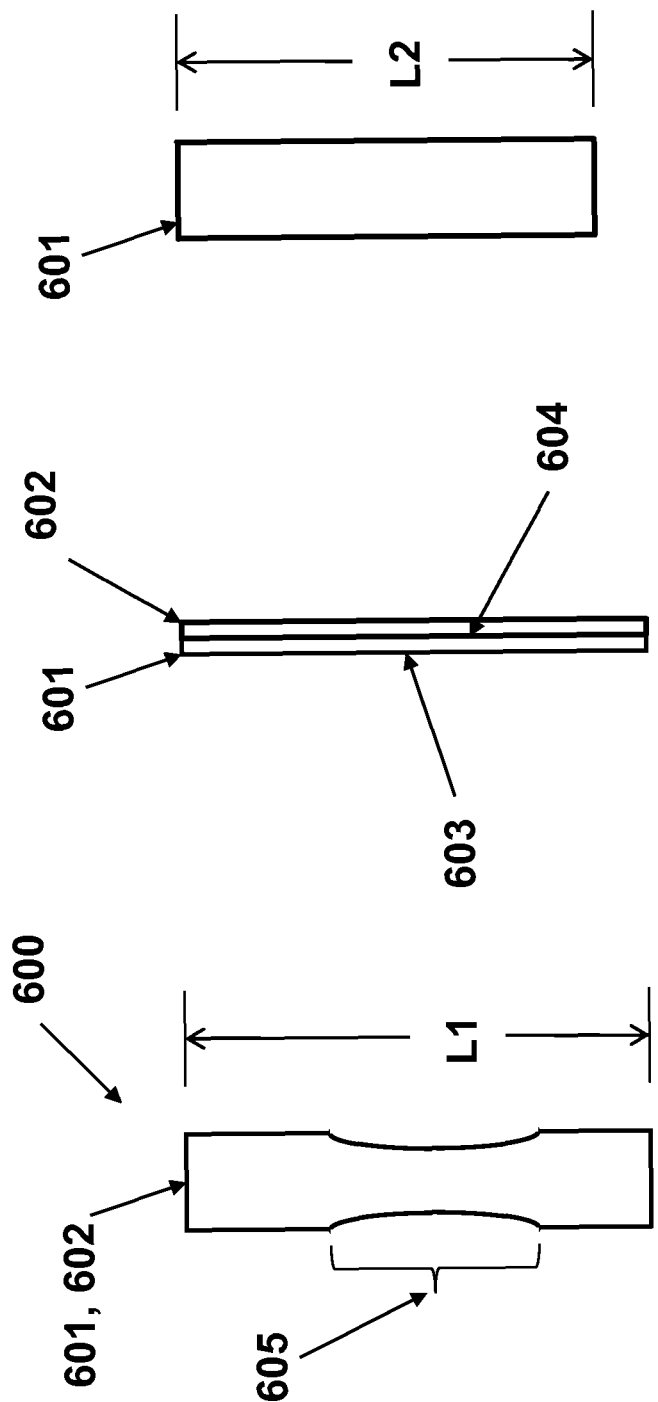

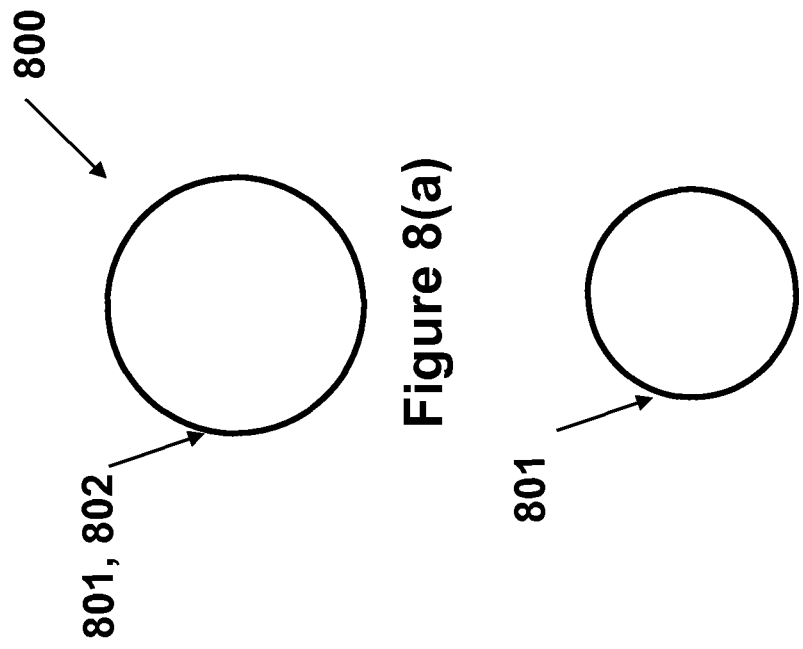
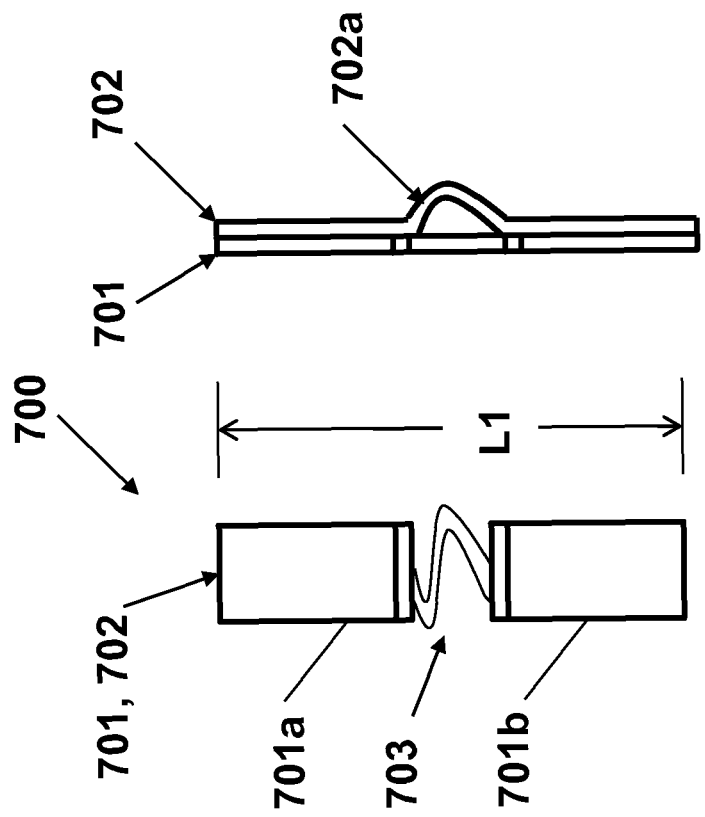

SHAPE AND PRESSURE ADJUSTABLE DRESSING

BACKGROUND

1. Field of the Invention

The present invention relates generally to dressings, and more specifically to shape and pressure adjustable dressings.

2. Prior Art

In many situations, dressings are desired to apply a certain amount of pressure on a wound or to apply a certain amount of force to close a wound or keep it closed, even over time as inflammation subsides. In other situations, it may be desired to increase the pressure or force over time to assist healing without a change in the dressing. In yet other situations it may be desirable to vary the pressure or force distribution over time. However, the currently available materials used for dressing wounds are difficult if not impossible to be used to achieve the above results in general, and to achieve it with ease and in a reliable manner in particular, even with the use of such aids as elastic components or tension fixtures.

In other situations, the dressing may be required to cover certain surfaces over the body that due to the shape of the surfaces, it may be difficult to make a close fit and even more difficult to apply pressure to the surface and sustain the applied pressure over time. In such situations, the dressing has to not only conform to the covered surfaces, but at the same time may have to provide a certain pattern of pressure or force to achieve certain goals.

A need therefore exists for a method to construct dressings that can be readily applied to the desired area, and then have the capability of its shape to be varied and/or apply a desired pattern of pressure or force to the covered area. The disclosed methods of varying the shape of the component just before use, is also advantageous in many applications since it can be used to reduce the size of the required packaging, e.g., a blister shaped component may be initially stored as a relatively flat sheet and then be turned to a blister just before application to the patient's skin.

SUMMARY

It is an object of the present invention to provide methods and/or dressings that: a) can be readily applied to a desired area, including areas that are hard to cover due to their shape and geometry; b) can be manipulated to change its shape in a predetermined manner (before or after its application); c) can be made to apply pressure (or a pulling force) to the covered area; and/or d) can be made to apply a force, for example an opening or closing force, in certain direction to the covered area.

Accordingly, a dressing for covering a wound is provided. The dressing comprising: a first component having a first shape with a first length; a second component releasably attached to a first surface of the first component to maintain the first component in a second shape different from the first shape, the second shape having a second length longer than the first length; and an adhesive disposed on a surface of the first component different from the first surface for attaching the first component to the wound such that the second component can be released from the first component to allow the first component to take the first shape to apply a pressure to portions of the skin surrounding the wound to close the wound.

The first and second dimensions can be a length in a single direction.

The first and second dimensions can be a length in more than one direction.

The change in shape can be due to at least a portion of the first component being formed of an elastic material capable of elastically deforming from the first shape to the second shape.

The change in shape can be due to one or more biasing members disposed between first and second portions of the first component.

The second component can include a portion for facilitating its removal from the first component. The portion can comprise a looped portion.

The first component can further comprise one of a medicament and gauze.

Also provided is a method for applying pressure to skin with a dressing. The method comprising: adhering at least a portion of the dressing to the skin; and subsequent to the adhering, changing the shape of the dressing by releasing a member from the dressing to allow the dressing to change the shape of the dressing such that the changed shape applies pressure to the skin; wherein the changing of the shape of the dressing comprises shortening at least on dimension of the dressing such that a wound on the skin is at least partially closed.

The at least one dimension can comprise two or more dimensions.

The shortening of the at least one dimension of the dressing can comprise elastically deforming a material forming at least a portion of the dressing.

The shortening of the at least one dimension of the dressing can comprise elastically biasing first and second portions of the dressing.

BRIEF DESCRIPTION OF THE DRAWINGS

These and other features, aspects, and advantages of the apparatus and methods of the present invention will become better understood with regard to the following description, appended claims, and accompanying drawings where:

FIG. 1(a) illustrates a first embodiment of a dressing having a first layer and a second layer.

FIG. 1(b) illustrates the dressing of FIG. 1(a) in which the first and second layers are separated.

FIG. 1(c) illustrates the first layer of FIG. 1(b) after the second layer has been separated therefrom.

FIG. 2(a) illustrates the dressing of FIG. 1(a) attached to the surface of skin.

FIG. 2(b) illustrates the dressing of FIG. 2(a) after the second layer has been removed.

FIG. 3(a) illustrates two component sheets of a second embodiment of a dressing.

FIG. 3(b) illustrates the two component sheets of FIG. 3(a) attached into an assembly.

FIG. 3(c) illustrates one of the components of FIG. 3(b) attached to the skin of a patient and the other of the components separated therefrom.

FIG. 5(a) illustrates a top view of yet another embodiment of a dressing.

FIG. 5(b) illustrates a side view of the dressing of FIG. 5(a) when at a temperature lower than a threshold temperature.

FIG. 5(c) illustrates the dressing of FIGS. 5(a) and 5(b) attached over a cut in skin.

FIG. 5(d) illustrates the dressing of FIG. 5(c) after the dressing has attained a temperature greater than the threshold temperature to close the cut in the skin.

FIG. 6(a) illustrates a top view of yet another embodiment of a dressing.

FIG. 6(b) illustrates a side view of the embodiment of FIG. 6(a).

FIG. 6(c) illustrates the dressing of FIGS. 6(a) and 6(b) after the second layer has been removed.

FIG. 7(a) illustrates a top view of a variation of the embodiment of FIG. 6(a).

FIG. 7(b) illustrates a side view of the embodiment of FIG. 7(a).

FIG. 8(a) illustrates a top view of another variation of the embodiment of FIG. 6(a).

FIG. 8(b) illustrates the dressing of FIGS. 8(a) after the second layer has been removed.

DETAILED DESCRIPTION

Figure 4A:
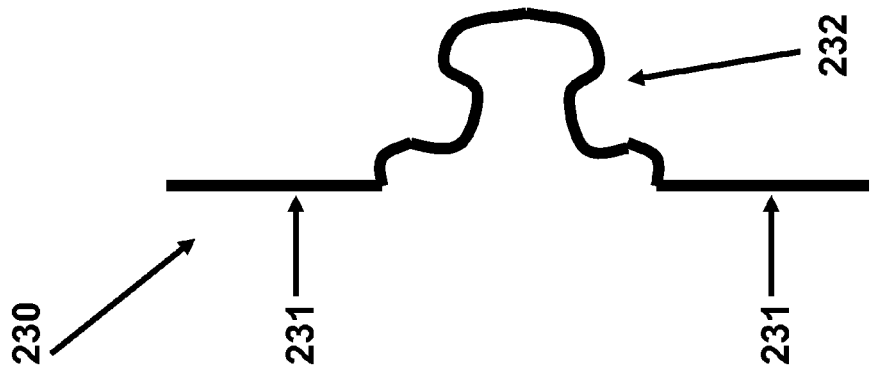
FIG. 4(a) illustrates another embodiment of a dressing.

A schematic of a basic design based on a first embodiment is shown in the FIGS. 1(a) to 1(c). In FIG. 1(a), the cross-section of a plane assembly 100 is shown, and consists of a first layer 101 and a second layer 107. The two layers are attached together using any methods known in the art, such as with adhesives, so that the user could readily separate them. The layer 101 consists of components 102 and 104, which are attached together with an intermediate component 103. Similarly, the components 104 and 106 are attached together with an intermediate component 105. The components 102, 104 and 106 are considered to be relatively devoid of internal stresses, while the components 103 and 105 have been originally shaped as shown in FIG. 1(c), but have been elastically flattened and held in the flattened configuration by the component 107, as shown in FIG. 1a, to form the assembly 100. Obviously, if the component (layer) 107 is separated from the assembly 100, as shown in FIG. 1(b), the components 103 and 105 would return to their original shape, and the layer 100 will take the shape shown in FIG. 1(c).

The first layer 101 can be formed of any material which can be fabricated into a certain (original) shape and elastically deformed into another shape, such as a plastic or metal or combination thereof. Furthermore, plate 107 can be formed of any material rigid enough to prevent the first layer 101 from taking the original shape while attached to the first layer.

In the schematic of FIGS. 1(a)-1(c), the assembly 100 is shown to be in the shape of a flat plate. It is, however, appreciated by those skilled in the art, that the assembly may form a curved surface; more stressed (preloaded or elastically deformed) and essentially unstressed (preloaded or elastically deformed) components may be used in the assembly; and in their unstressed state, the stressed (preloaded or elastically deformed) component(s) may have been constructed to assume a variety of shapes (configurations), including complex shapes and curvatures. In general, upon the removal of the constraining component(s), the stressed (preloaded or elastically deformed) component(s) will tend to return to their unstressed (natural) state. It is appreciated that the stressed component(s), while tending to return to their unstressed (natural) state (shape or configuration), may still retain part of their induced internal stresses.

The dressing assembly 100 may be applied to the body surface 110, e.g., via an adhesive layer on the free surface of the layer 101 (not shown), as can be seen in FIG. 2(a). Once the assembly 100 is securely attached to the body surface, the layer 107 (wholly or partially) is removed. FIG. 2(b) shows the case in which the layer 107 is removed. At least part of the preloading stresses in the components 103 and 105 are then released. As a result, the layer 101 tends to its natural (stress-free) state. The components 102 and 106 are then pulled towards each other in the direction 112, and the underlying skin is pulled together. Thereby if a cut was present in the section of the skin 111 between the 102 and 106 components, the above action would tend to force it closed. The component 104 of the layer 107 is also pushed away from the skin.

In the schematics of FIGS. 1(a)-1(c), for the sake of simplicity, only two distinct layers are used and only one of the layers is provided with the preloaded components. However, more than one layer can be utilized, and layers with partially preloaded components may also be used to construct the dressing components. It is also possible to construct devices that are constructed with at least two layers of fully preloaded components. In addition, the final assembly (assembly 100) does not have to be flat, and may assume any appropriate shape and configuration as dictated with the particular application.

It should also be noted that in the schematics of FIGS. 1(a)-1(c), and in the remaining illustrations, only living joints are illustrated at discontinuities in the first layer 101. It is, however, appreciated that regular joints, such as pin joints and/or sliding joints, may also be used in the construction of the present devices.

Another embodiment of a dressing is shown schematically in FIGS. 3(a)-3(c). The dressing assembly 200 shown in FIG. 3(b), consists of at least two components (sheets) 201 and 202, which in their free (natural) form are curved as shown in FIG. 3(a). The dressing 200 is assembled by deforming the components 201 and 202 to their assembly configuration and attaching them together, preferably using adhesives, to achieve their final (assembled) configuration. In FIG. 3(a), and for the sake of simplicity, the two components 201 and 202 are shown to be deformed in a symmetrical manner, which upon bending in the directions 203 and 204, respectively, could be nearly flattened to their final shape in the assembly. In this particular case, since the two components 201 and 202 are considered to be identical and with symmetrical initial deformation, then upon their assembly after being flattened would assume a flat configuration. It is readily seen that by using two or more components with varying shape, and/or size, and/or materials, and/or initial (free or natural) configuration, one could construct infinite number of assemblies, which upon partial or full removal of one or more of the components, the desired final shape, size, configuration, and when appropriate applied force (moment or torque) to the attached member, could be achieved.

In certain assemblies, it may be necessary to use less strong adhesives for assembling certain components of the assembly for reasons such as ease of removal. In such cases, it may be necessary to provide mechanical locking action, such as by bending sides or corners of one component over the other, or by using attachment methods such as sewing or stapling or by using one or more clipping elements, etc., which is/are readily removable before applying the dressing to the patient or following its application. FIG. 3(c) illustrates the dressing 200 attached to a surface of the skin and sheet 202 removed, in which case sheet 201 is deformed towards its original shape and the skin takes the shape of the sheet 201 and is pulled together.

Figure 4B:
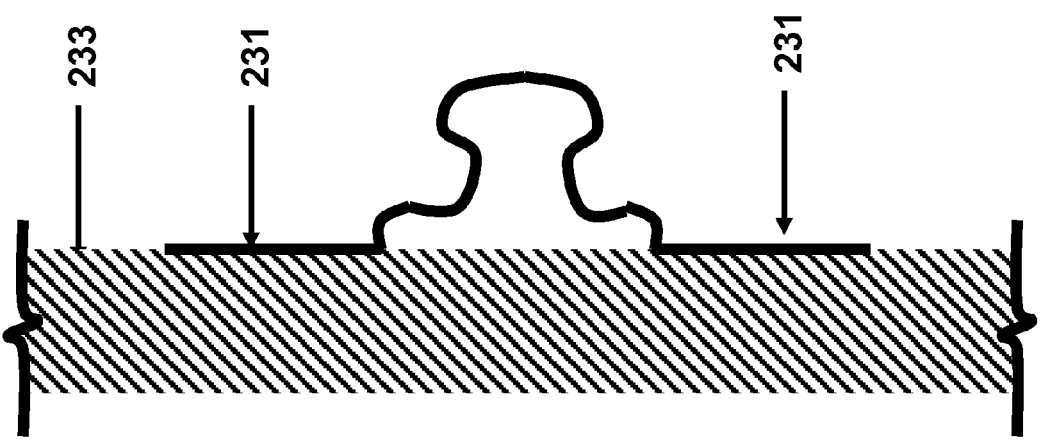
FIG. 4(b) illustrates the dressing of FIG. 4(a) attached to skin of a patient.
Figure 4C:
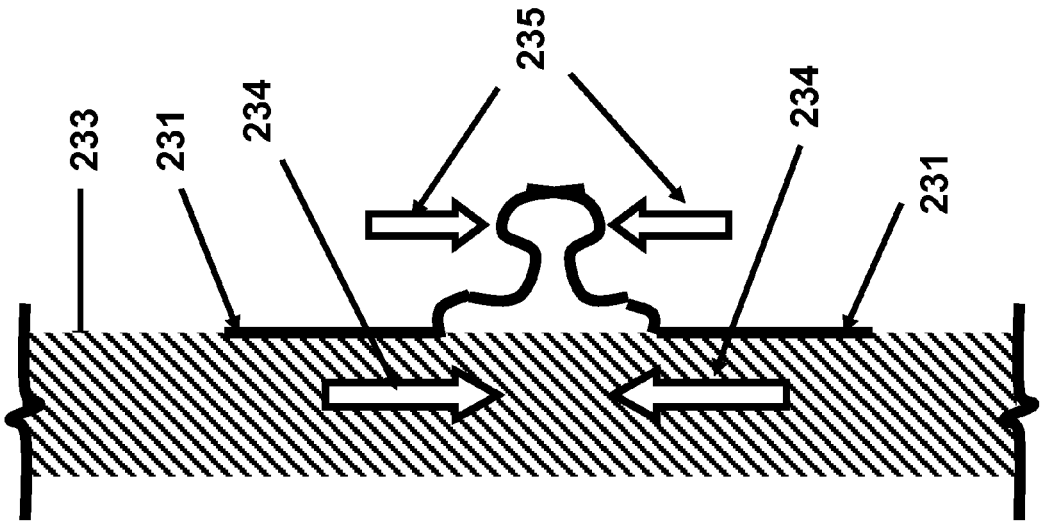
FIG. 4(c) illustrates the dressing of FIG. 4(b) being compressed together.

Yet another embodiment of a dressing is shown in FIGS. 4(a)-4(c). The schematic of the side view of a plate formed with two flat sides 231 and a middle side 232, forming a simple example of a dressing element 230 is shown in FIG. 4(a). The adhesives that are preferably provided on these surfaces may then apply the dressing element 230 to the surface of the skin 233 as shown in FIG. 4(b), via the surfaces 231. The part 232 is then compressed together (or twisted or otherwise deformed) in the direction of bringing the surfaces 231 together (direction 235), such as with a tie-wrap, string wire or the like. As a result, the underlying skin is pulled together in the direction 234, thereby closing a wound or providing a desired compressive pressure, or in short the desired effect.

In all the disclosed embodiments, appropriate dressing components such as gauzes, medications, etc., may be disposed (preferably in the middle regions) of the dressing assemblies to cover the wound. Ventilation or drainage ports may also be provided when appropriate in these regions. Elastic or removable elements may also be provided over or around such regions for administering medication. In certain cases, it may also be desirable to construct one or more components of the assembly with transparent materials so that the affected region could be observed.

In addition, in all the disclosed embodiments, the applied pressure or would closing action of the dressing element may be increased or decreased over time by removing, e.g., a larger piece of the shape/configuration affecting components or by further deformation of the shape/configuration affecting components. You can also vary the pressure applied by the dressing so that the skin can be "pushed" and "pulled."

Referring now to FIGS. 5(a)-5(d), the component 101, 201 disposed on the skin can be formed, at least in part, of a shape memory material. Thus, when disposed on the skin, the component 101, 201 can change shape, in whole or in part, due to a shape memory effect upon being heated by the temperature of the skin to at or above a transition temperature of the shape memory material. Such materials are well known in the art and can be either metals or plastics which exhibit the shape memory effect. A dressing having such a configuration can eliminate the second component 107, 202 since the shape memory material can take one form, such as flat, at a first temperature (FIG. 5(b)) and take another shape, such as that shown in FIG. 5(d) at a second temperature. Thus, the plate 107, 202 is not needed to maintain the sheet 101, 201 in the shape shown in FIGS. 5(a) and 5(b). In this configuration, the dressing component can be shaped as shown in FIG. 5(d) when subjected to a temperature above the threshold temperature (e.g., body temperature) and can be flat when subjected to a temperature lower than the threshold temperature.

This dressing has particular utility when used as a butterfly type dressing for closing wounds that may otherwise require stitches. In this regard, the plan or top view shape of the dressing 101, 201 can be shaped like a conventional butterfly bandage having a narrowed section in the middle thereof, as shown in FIG. 5(a). Once placed over a cut 300 on the skin 302, such as with adhesive on a face 303 of the dressing 101, 201, as shown in FIG. 5(c), preferably disposed on the surface outside of the narrowed portion. After the dressing 101, 201 is warmed by the body heat of the skin, the shape memory material changes its shape to another shape, such as that shown in FIG. 5(d) to close the cut 300 by applying pressure in the direction of arrows 304. The portion of the dressing 101, 201 contacting the cut 300 may have a gauze and/or a medicated layer.

In a variation of such embodiment, the shape memory material dressing can be kept cool and applied to the skin while it is cold. Then the room temperature will activate it to change its shape so that you are not limited to activation with body temperature, which might be very close to the environmental temperature.

Other active materials that could be employed for the dressing could be active polymers, which would require a voltage to get them to pull.

Another embodiment will now be described in which the shape of the dressing changes after release of a release member, similar to those described with regard to FIGS. 1-4, except that the shape change is a change in length of the dressing. FIG. 6(a) illustrates a dressing for a wound, generally referred to by reference numeral 600. The dressing 600 includes a first component 601, which can be a first layer, having a first shape with a first length L1. The dressing 600 further includes a second component, which can be a second layer, which is releasably attached to a first surface 604 of the first component 601 to maintain the first component 601 in a second shape different from the first shape. In the embodiment of FIGS. 6(a)-6(c), the second shape has a second length L2 which is longer than the first length. An adhesive is disposed on a surface 603 of the first component 601 different from the first surface 604 for attaching the first component 601 to the wound such that the second component 602 can be released from the first component 601 to allow the first component to take the first shape to apply a pressure to portions of the skin surrounding the wound to close the wound.

Thus, the dressing 600 is applied to the skin by adhering the surface 603 to the skin while the first component 601 is constrained into the first shape have a length L1. The second component 601 is then removed from the first component 601 to remove such constraint and allow the first component 601 to take the second shape having a shorter length L2, thus applying pressure to the skin which tends to close a wound.

The first component 601 can be formed of any material which can be fabricated into the first shape and elastically deformed into the second shape, such as an elastic material which can elastically stretch in at least one direction. Furthermore, the second component 602 can be formed of any material rigid enough to prevent the first component 601 from taking the second shape while attached to the first component 601.

In addition to an elastic material, the change of shape from the first length L1 to the second length L2 can be achieved by any other means for elastically biasing the first component 601 into the first length L1, such as one or more elastically deformed members attached at one end to a first portion of the first component and attached at a second (or another end) to a second portion of the first component. An example of such, referred to by reference numeral 700, is illustrated in FIGS. 7(a) and 7(b) having a biasing member 703 attaching first and second portions 701a, 701b of the first component 701. Such biasing member 703 can be of any material, such as plastic or metal that can elastically deform into the first shape and back to the second shape. FIG. 7(b) illustrates the second component 702 having a loop portion 702a adjacent to the biasing member 703 for facilitating removal of the second component.

The first component can have such elastic properties throughout the length L1 or a portion thereof, such as portion 605 which is adjacent to the wound. Also, although the embodiment of FIGS. 6(a)-6(c) is described with regard to a shape change in one direction, such shape change can occur in a different direction (such as perpendicular to the direction shown) or in more than one direction (such as in the direction shown and a direction perpendicular thereto). An example of such is shown in FIGS. 8(a) and 8(b), referred to by reference numeral 800, in which the first shape of the first component is a first diameter (shown in FIG. 8(a)) and the second shape is a second diameter smaller than the first diameter (shown in FIG. 8(b)). Such a variation is useful to apply pressure to the skin in more than one direction to close a wound, such as a puncture wound.

As discussed above, the first component can further include one or more of a medicament and gauze. As also discussed above, the two components can be attached together using any methods known in the art, such as with adhesives, so that the user could readily separate them and more intermediate components (not shown) can be used.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A dressing for covering a wound, the dressing comprising:
    a first component having a first shape with a first dimension;
    a second component releasably attached to a first surface of the first component to maintain the first component in a second shape different from the first shape, the second shape having a second dimension longer than the first dimension; and
    an adhesive disposed on a surface of the first component different from the first surface for attaching the first component to the wound such that the second component can be released from the first component to allow the first component to take the first shape to apply a pressure to portions of the skin surrounding the wound to close the wound.

2. The dressing of claim 1, wherein the first and second dimensions are a length in a single direction.

3. The dressing of claim 1, wherein the first and second dimensions are a length in more than one direction.

4. The dressing of claim 1, wherein the change in shape is due to at least a portion of the first component being formed of an elastic material capable of elastically deforming from the first shape to the second shape.

5. The dressing of claim 1, wherein the change in shape is due to one or more biasing members disposed between first and second portions of the first component.

6. The dressing of claim 1, wherein the second component includes a portion for facilitating its removal from the first component.

7. The dressing of claim 6, wherein the portion comprises a looped portion.

8. The dressing of claim 1, wherein the first component further comprises one of a medicament and gauze.

9. A method for applying pressure to skin with a dressing, the method comprising:
    adhering at least a portion of the dressing to the skin; and
    subsequent to the adhering, changing the shape of the dressing by releasing a member from the dressing to allow the dressing to change the shape of the dressing such that the changed shape applies pressure to the skin;
    wherein the changing of the shape of the dressing comprises shortening at least one dimension of the dressing such that a wound on the skin is at least partially closed.

10. The method of claim 9, wherein the at least one dimension comprises two or more dimensions.

11. The method of claim 9, wherein the shortening of the at least one dimension of the dressing comprises elastically deforming a material forming at least a portion of the dressing.

12. The method of claim 9, wherein the shortening of the at least one dimension of the dressing comprises elastically biasing first and second portions of the dressing.

* * * * *